United States Patent [19]

Gilbert

[11] 4,003,381
[45] Jan. 18, 1977

[54] CRICOTHYROSTOMY INSTRUMENT

[76] Inventor: Max I. Gilbert, 9612 N. Military Trail, Palm Beach Gardens, Fla. 33407

[22] Filed: Apr. 30, 1975

[21] Appl. No.: 573,223

Related U.S. Application Data

[62] Division of Ser. No. 483,727, July 3, 1974, Pat. No. 3,906,956.

[52] U.S. Cl. .................................. 128/305.3
[51] Int. Cl.² ................................. A61B 17/24
[58] Field of Search ...................... 128/351, 305.3

[56] References Cited

UNITED STATES PATENTS

| | | | |
|---|---|---|---|
| 3,570,498 | 3/1971 | Weighton | 128/347 |
| 3,721,233 | 3/1973 | Montgomery et al. | 128/351 |

FOREIGN PATENTS OR APPLICATIONS

| | | | |
|---|---|---|---|
| 408,292 | 9/1966 | Switzerland | 128/351 |

*Primary Examiner*—Channing L. Pace
*Attorney, Agent, or Firm*—Steele & Petock

[57] ABSTRACT

An instrument for emergency laryngeal-tracheal operations hereinafter referred to as a cricothyrostomy instrument which includes a cricothyrostomy tube of generally L-shaped configuration with the tube having an access opening through which a cutting instrument may be inserted to penetrate the laryngeal-tracheal wall, preferably the cricothyroid membrane, thus enabling the tube to be inserted in the trachea of the individual to permit an airway to be cleared.

4 Claims, 6 Drawing Figures

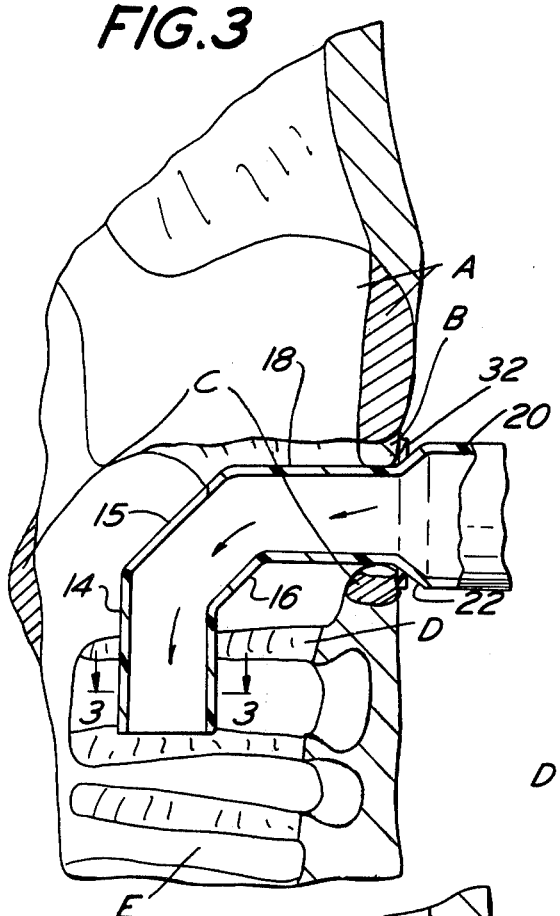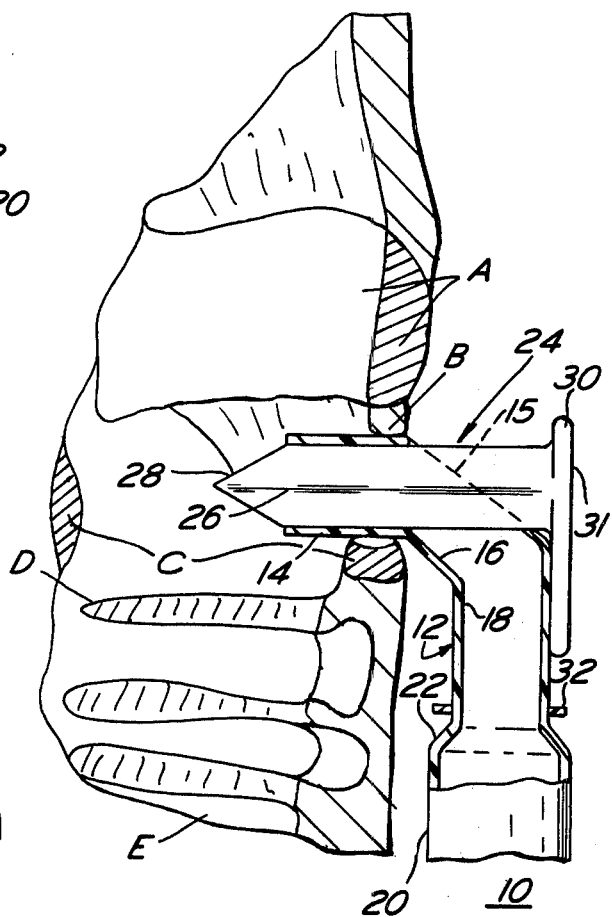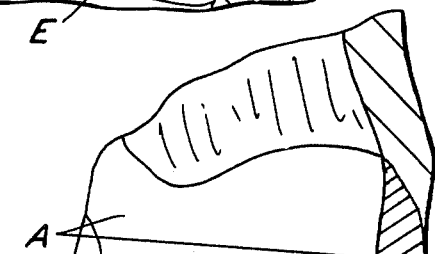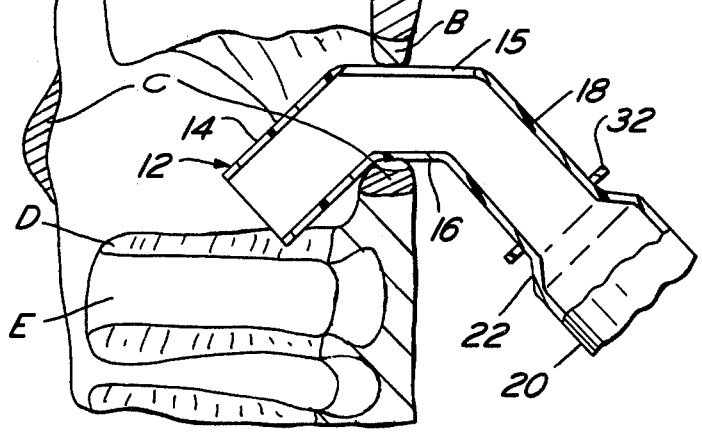

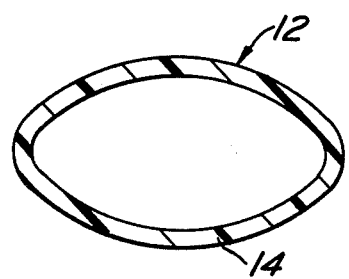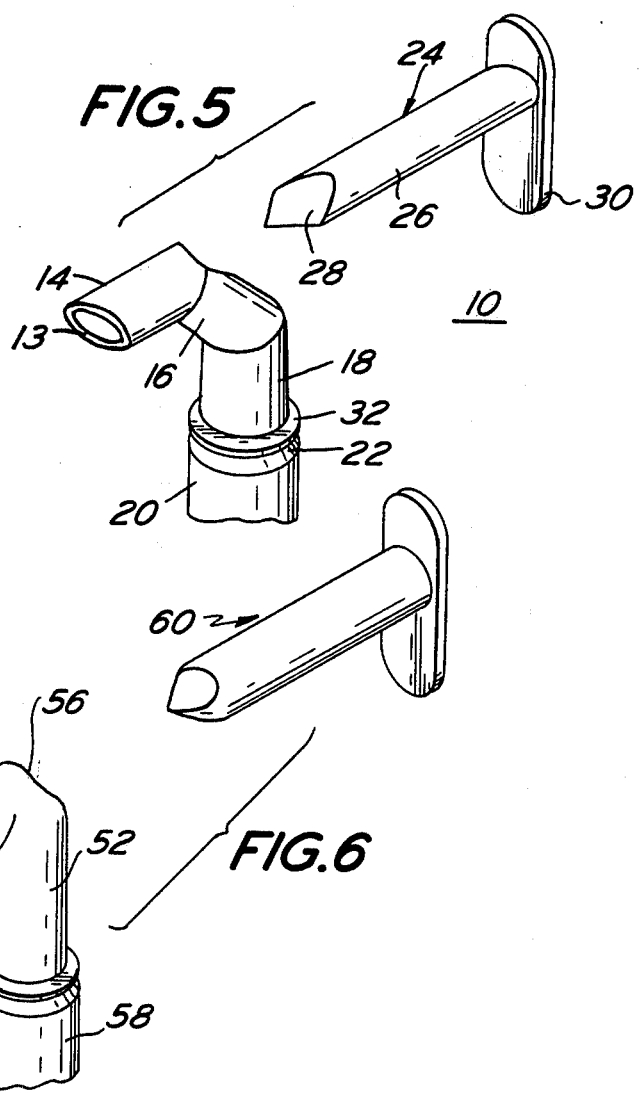

CRICOTHYROSTOMY INSTRUMENT

CROSS REFERENCE TO RELATED APPLICATION

This application is a division of applicant's prior copending application Ser. No. 483,727, filed July 3, 1974, which is now U.S. Pat. No. 3,906,956 which issued on Sept. 23, 1975.

BACKGROUND OF THE INVENTION

1. Field of the Invention

The subject invention relates generally to the performance of tracheotomies and cricothyrostomies and discloses an instrument which, while it can be used advantageously in the performance of either one of the above surgical emergencies, is particularly adapted for performing cricothyrostomies.

Acute respiratory distress is a life threatening situation wherein minutes and seconds literally mean the difference between life and death. By either performing an emergency tracheotomy or cricothyrostomy, the latter differing from a tracheotomy in that the entry is made through the cricothyroid membrane, an airway can be opened to a person's trachea to alleviate the acute onset of anoxia or hypoxia where mouth to mouth resuscitation may be impractical of ineffective.

There is a demand for such instruments not only for the performance of operations under ideal surgical conditions but also where a trained surgeon is not available. Paramedics, nurses, ambulance and rescue personnel, and the like, often are confronted with life threatening situations where every minute counts. Present day instruments require perfected techniques and expertise which may be gained only through extensive experience and thus, many in life saving situations are inhibited from taking responsibility where positive unhesitating action is critical to success.

Prior Art

In the past, devices used for surgically gaining access to a person's trachea primarily have been tracheotomy instruments of a standard configuration. The most widely used instruments comprise an arcuate hollow tube which is used in conjunction with an arcuate trocar instrument extendable therethrough which is used to make the incision. Various types of such instruments are shown in U.S. Pat. Nos. 2,865,374 — Brown et al, 2,991,787 — Shelden et al and 3,556,103 — Calhoun. As shown in Brown et al and Shelden et al, the arcuate trocar instrument has a cutting portion with blade elements perpendicular to one another to cut a cruciate incision. One of the disadvantages of such an instrument when used in surgical procedures, is that an excessive amount of bleeding is likely to result as contrasted to where a simple linear penetration is achieved.

Further, the arcuate structure of the tube and trocar of the prior art patents is significantly deficient in at least one very important phase of its use. The instrument is extremely difficult to handle because of the shape of the trocar giving rise to the necessity to insert it very slowly and precisely as the incision is made. Improper angulation during penetration is likely to result in the cutting of the posterior tracheal membrane which is very soft tissue.

In U.S. Pat. No. 3,476,113 — Tarsitano, a cricothyrostomy set is disclosed which is used to penetrate a cricothyroid membrane and to provide access to the trachea at this location. While there are advantages which will be discussed in making entry at this location, the Tarsitano device does not disclose an instrument which may be actually inserted into the mid tracheal lumen to provide the type of access to a person's trachea where a substantial amount of air may be quickly provided for emergency purposes.

Summary of the Invention

Accordingly, it is an object of the subject invention to provide a cricothyrostomy instrument which is uniquely designed for use to penetrate the cricothyroid membrane and to be insertable into the patient's trachea to provide an emergency airway.

It is another object of the subject invention to provide a cricothyrostomy instrument which may be used by relatively untrained and unskilled medical or lay personnel for performing cricothyrostomies and in the alternative, tracheotomies in emergency situations.

It is another object of the subject invention to provide a cricothyrostomy instrument which has improved airway means by having dual openings in the portion of the tube which will be inserted into the patient's trachea.

It is yet another object of the subject invention to provide a cricothyrostomy instrument in which a straight cutting instrument or trocar instrument may be used to provide ease and safety during penetration and to reduce the likelihood of improper angulation.

It is still another object of the subject invention to provide a cricothyrostomy instrument which is uniquely designed in cross-section to take advantage of the most advantageous position of entry into a person's trachea.

It is yet another object of the subject invention to provide a cricothyrostomy instrument which may be effective with or without the use of a positive pressure unit.

It is but one more object of the subject invention to provide a cricothyrostomy instrument which has a sliding adaptor to prevent a shifting in position once the instrument is inserted.

It is one more object of the subject invention to provide a cricothyrostomy instrument in which the cutting or trocar instrument has an improved cutting blade to minimize bleeding and other effects during penetration.

In accordance with the above objects, a laryngeal tracheal or cricothyrostomy instrument is provided which includes two major components. The first is a cricothyrostomy tube which is generally L-shaped and which has an access opening in the proximity of the vertex angle of the L to permit entry of the second major component which is a straight knife or cutting instrument referred to as a trocar. While the instrument may be used anywhere in the laryngeal-tracheal region, it is specifically designed for use in the cricothyroid space and is of oval configuration to better take advantage of anatomical characteristics of all patients. The cricothyroid space is the most superficial area of the laryngeal-tracheal region which makes it the most accessible approach to use and one which is easily located by prominent easily palpated characterisitcs even in obese patients. In this area, there is less likelihood of hemorrhage and since it is superficial, there is no deep soft tissue damage during penetration.

The use of a straight trocar or knife increases the control over the unit and enables paramedics and other individuals to use the instrument in emergency situations. Once penetration is achieved, the tube, because of its general configuration, may be easily slid into the trachea preferably through the cricoid space since another advantage of this location is in the event the instrument contacts the posterior membrane, there is additional cricoid cartilage to prevent the instrument from penetrating the posterior portion of the trachea. After the tube is inserted and enters the trachea, the knife member can be easily withdrawn. When the tube is advanced, the dual openings in the tube through which the knife member passed, can be positioned within the tracheal portion to increase the air flow.

Brief Description of the Drawings

FIG. 1 shows the cricothyrostomy instrument as it is penetrating through the cricothyroid membrane of a patient;

FIG. 2 shows the cricothyrostomy tube as it is being advanced after the knife member has been withdrawn;

FIG. 3 discloses the cricothyrostomy tube in position after having been adjusted to its fully operative position;

FIG. 4 is a cross-sectional view of a portion of the cricothyrostomy tube taken through section lines 4—4 of FIG. 3;

FIG. 5 is a perspective view of the instrument showing the cutting member removed from the cricothyrostomy tube; and FIG. 6 is a perspective view of a cricothyrostomy tube of an alternate embodiment.

Detailed Description

With reference to FIGS. 1-3, the laryngeal-tracheal region of the anatomic structure of a patient is shown. The thyroid cartilage A is directly above the cricothyroid membrane B and the cricoid cartilage C. The trachea D is shown surrounded by tracheal rings E.

The laryngeal-tracheal or cricothyrostomy instrument is shown generally as 10 and comprises a cricothyrostomy tube member 12 and a cutting instrument 24 which are seen in perspective in FIG. 5. The tube 10 is in part an ovoid hollow member having three segments 14, 16 and 18 whith each succeeding segment being approximately 45° to the preceeding segment. In other words, each succeeding segment deviates from a straight line by 45°, with succeeding segments subtending an obtuse angle of approximately 135°, as most clearly shown in FIGS. 2 and 3. An overall L-shaped configuraton thus results. The opening at the end of tube 14 will be designated as the advance opening 13. At the opposite end the tube 10 may terminate in a cylindrical portion 20 with portion 22 being transitional. This enables the tube 10 to be adaptable to standard positive pressure units (not shown) which may be utilized to provide air under pressure. An access entry way 15, the purpose of which will be subsequently described, is located in the tube 12 and may be entirely within middle segment 16 as shown in FIG. 1. The ovoid shape of segments 14, 16 and 18 of the tube is to be emphasized as is shown in FIG. 4 and is important since the cricothyroid space is of similar configuration.

With further reference to FIGS. 1 and 5, the cutting instrument or trocar 24 is shown as comprising an ovoid cutting member 26 which terminates in a cutting edge 28. At the opposite end from the cutting edge 28, a guiding portion 30 is disclosed which serves as both a guiding means with surface 31 serving as a thumb rest; and a restraining means to limit the extent of entry of the cutting member 26 into tube 10.

With further reference to FIGS. 1–4 and 5, a restraining member 32 which may be adjustable, is used to position the cricothyrostomy tube 10 at a desired operational position once the insertion is accomplished. The restraining member 32 may be a friction slide device as shown in FIG. 1 or in the alternative, it may have adjustable screw or clamp means. Furthermore, the restraining member 32 may be eliminated and the transition portion 22 may serve as a guard to prevent the instrument from being inserted too far into the patient. As shown in FIG. 2, the cutting instrument 24 has been withdrawn and the tube is being advanced. While the tube is functional in FIG. 2, the ultimate fully operational position is shown in FIG. 3.

In using the cricothyrostomy instrument and with reference first to FIG. 1, the cutting instrument 24 is inserted through access opening 15 and through the first segment 14 of the tubing, projecting slightly outwardly of advance opening 13 (see FIG. 5). Penetration is achieved with the first segment 14 and cutting member 26 held perpendicular to the cricothyroid membrane. A "pistol grip" may be used with the thumb resting on thumb surface 31 of the cutting instrument 24 while the fingers grip segment 18 of the cricothyrostomy tube 12. With the neck extended, penetration of the cricothyroid membrane is achieved and the instrument 10 advanced to the first angulated segment 16 of the tube. The cutting instrument 24 is then withdrawn through the access opening 15 in the second angulated segment 16 and it is at this time that the patient may begin to breathe. The cricothyrostomy tube 12 is then lifted and guided gently as the angulated portion 16 is inserted further with the first segment 14 being urged downwardly into the trachea as shown in FIG. 2. Next, the third segment 18 is likewise advanced to the point where the first segment 14 of the tube is approximately in the mid-trachea as shown in FIG. 3. It is to be noted that each segment is inserted as it is perpendicular to the neck. The optional adjustable end 32 may be used to secure the tube 12 to maintain the position as shown in FIG. 3.

A standard positive pressure device may then be connected to tube portion 20 although this may not be critical for survival. It is noted at this operational position both the advance opening 13 and access entry way 15 are within the trachea to provide dual openings therein to increase the air flow to the patient. Either the restraining member 32, or the transitional area 22 may be used to secure the instrument at its operational position. The cricothyroid anatomical configuration is of generally ovoid configuration and accommodates the tube 12 with a minimum of hemorrhaging due to the simple linear slit that was made by the cutting edge 28.

Thus, it is advantageous to use the instrument in the cricothyroid area and optimum benefits are obtained with the use of the ovoid configuration since it takes full advantage of the natural anatomical surrounding structure and permits the largest airway possible. Effectively, the cross-sectional area is roughly twice that of the cross-sectional area of a circular cylinder of the largest diameter that the circothyroid area could receive. Since during stress conditions, a patient's need for air increases drastically, the advantage of utilizing tubing of maximum cross-sectional area can be readily appreciated. In this light, it will be appreciated that the subject instruments may be of various sizes to be best suited for patients having different physical size characteristics.

By using the instrument in the cricothyroid area, advantage is also taken of the posterior segment of the cricoid cartilage which is not easily penetrated, thus aiding in the prevention of damage to the laryngeal-tracheal wall and further reducing the possibility of delayed complications from penetration and infection. In addition, the cricothyroid space is the most superficial area of the laryngeal-tracheal region and is thus the most accessible approach. Tissue damage and the likelihood of hemorrhaging are also reduced in this area.

In an alternate embodiment shown in FIG. 5, the cricothyrostomy tube 48 has been modified and as shown is L-shaped with components 50 and 52 joining at essentially a right angle with optional angle portion 54 being rounded to facilitate the full insertion of the tube 48. An access opening 56 is shown in the vertex region which accommodates a cutting instrument 60 similar to that shown in FIGS. 1 and 5. The modified tube 48 and its accommodating cutting member may be circular in cross-section, as shown, however, if the instrument is to be used in the cricothyroid region, it preferably should be of ovoid configuration. A protective widened end 58 similar to that of the previous embodiment may be employed but is optional if other restraining means and positive pressure receiving means are utilized.

While a wide range of materials may be used for the above embodiments of the tube and cutting member, the use of polyethylene or equivalent for the tube and metal such as stainless steel for the cutting member is contemplated.

While various embodiments of the invention have been shown and described, it will be understood that other modifications may be made. The appended claims, therefore, are intended to define the true scope of the invention.

I claim:
1. A laryngeal-tracheal tube comprising:
   a first linear segment suitable for introduction through an incision into a patient's tracheal passage;
   a second linear segment angulated to said first segment, said first and second segments subtending an obtuse angle; and
   a third linear segment angulated to said second segment, said third and second segments subtending an obtuse angle, whereby said first segment and said third segment from an angle of approximately 90° with respect to each other and said third segment being suitable for positioning to extend through the incision in the patient's laryngeal-tracheal region whereby said first segment of said laryngeal-tracheal tube may be inserted through said incision and said second and third segments may be incrementally successively advanced to where said third segment is positioned so as to extend through said incision.
2. A laryngeal-tracheal tube in accordance with claim 1 wherein said first segment is ovoid in cross section.
3. A laryngeal-tracheal tube in accordance with claim 1 wherein said third segment is provided with a restraining member to prevent the laryngeal-tracheal tube from being inserted too far into the patient.
4. A laryngeal-tracheal tube in accordance with claim 1 wherein said second segment is provided with a side wall having an opening therein.

* * * * *